United States Patent [19]
Kelley

[11] 4,019,994
[45] Apr. 26, 1977

[54] PROCESS FOR THE PREPARATION OF AQUEOUS MAGNETIC MATERIAL SUSPENSIONS

[75] Inventor: Jack R. Kelley, Bellingham, Wash.

[73] Assignee: Georgia-Pacific Corporation, Portland, Oreg.

[22] Filed: Aug. 28, 1975

[21] Appl. No.: 608,463

[52] U.S. Cl. .......................... 252/62.52; 252/62.51; 252/62.53

[51] Int. Cl.$^2$ .................... G01N 27/82; H01F 1/00

[58] Field of Search ......... 252/62.51, 62.52, 62.53, 252/62.54

[56] References Cited

UNITED STATES PATENTS

| | | | |
|---|---|---|---|
| 2,304,308 | 12/1942 | Hurd | 106/308 S |
| 3,214,378 | 10/1965 | Hanneman | 252/62.52 |
| 3,586,630 | 6/1971 | Ingersoll | 252/62.54 |
| 3,634,252 | 1/1972 | Graham | 252/62.54 |
| 3,764,540 | 10/1973 | Khalafalla et al. | 252/62.55 |

*Primary Examiner*—F.C. Edmundson
*Attorney, Agent, or Firm*—Peter P. Chevis

[57] ABSTRACT

A process for the preparation of aqueous magnetic oxide suspensions is described.

15 Claims, No Drawings

PROCESS FOR THE PREPARATION OF AQUEOUS MAGNETIC MATERIAL SUSPENSIONS

This invention pertains to a process for the preparation of magnetic suspensions. More particularly it pertains to a process for the preparation of magnetic iron oxide or hydroxyoxide in an aqueous medium.

The technological advances made in the last few years have greatly increased the demand for magnetic materials. These advances have also created needs for magnetic materials of unique properties. Ferromagnetic solids such as metals, metal oxides, and alloys are by nature water-insoluble and considerable processing is required to obtain these materials in quasi-fluidic form which is necessary for certain applications. Stable suspensions of magnetite may be prepared by grinding magnetite, e.g. by ball milling, in a hydrocarbon such as heptane or kerosene in the presence of a dispersant as described in U.S. Pat. No. 3,215,572, Magnetic fluids may also be prepared by comminuting a non-magnetic iron compound to suspension particle size and converting the non-magnetic iron to ferromagnetic form as described in U.S. Pat. No. 3,764,540. Reimers, et al., in the Bureau of Mines Technical Progress Report No. 59, September, 1972, reported the preparation of magnetic fluids by precipitation of iron II and iron III hydrous oxides in aqueous medium and dispersion of the precipitate in organic carriers, such as kerosene, by using a dispersing agent such as oleic acid in the hydrocarbon. Dilute suspensions or sols of metal oxides in aqueous mediums may be prepared at concentrations of less than 1% by the method described in Great Britain Pat. No. 976,328. The process, however, is ineffective for the preparation of magnetic fluids in concentrations containing from about 5 to 30% by volume of the magnetic solids or materials. Dispersions of the magnetic materials in aqueous medium have been generally obtained by the preparation of the ferromagnetic suspension in a hydrocarbon base and then substituting the carrier. In U.S. Pat. No. 3,531,413 a substitution of carrier or solvent is described where flocculation of the magnetic material in the hydrocarbon solvent is first obtained by employing polymeric flocculating agents and then redispersing the flocculated particles in the new solvent. In the flocculation, the small particles of the magnetic material remain surface-coated with the hydrocarbon solvent and surfactant which is usually still compatible with the new solvent due to the small amount of hydrocarbon present.

It is, therefore, an object of this invention to provide a process for the preparation of a ferromagnetic fluid in an aqueous medium. A still further object is to provide an aqueous base magnetic fluid obtained by precipitation of the magnetic material in the aqueous medium. A still further object is to provide a process for the preparation of an aqueous magnetic fluid by the precipitation of magnetic iron oxide and/or iron hydroxyoxide.

The above and other objects are attained by the preparation of the magnetic iron oxide or iron hydroxyoxide in an aqueous medium in the presence of a sulfonated petroleum dispersant. The iron oxides are prepared by reaction of an iron compound at a pH in the range of 5.5 to 8 to form iron hydroxide which is then converted while in aqueous medium to the magnetic iron oxides or hydroxyoxides. By the process, suspensions of the magnetic iron composition in a concentration range of from 5 to 30 weight percent may be prepared. The sulfonated petroleum dispersant is present in an amount sufficient to disperse the magnetic iron oxide or hydroxyoxide composition. Usually the dispersant is used in an amount of from 1 to 20 weight percent of the solution, preferably from 5 to 10%.

The dispersant used is a petroleum sulfonate which is usually obtained upon treatment of a heavy petroleum oil fraction with sulfuric acid. The petroleum sulfonates used are anionic and are oil soluble. The product is readily available as the sodium salt which is obtained upon neutralization of the sulfonation mixture with caustic. Generally upon treatment of petroleum fractions with sulfuric acid only a portion of the petroleum is sulfonated with the unsulfonated oil being extracted by use of solvent. Also, the petroleum sulfonate may contain additives such as glycol ethers, glycol ether esters or treated with an oxidizing agent such as hypochlorite or dichromate to reduce the viscosity of the product. The oil-soluble petroleum sulfonates are often called "mahogany soaps" and may be used as obtained upon sulfonation of the petroleum and purified or treated to reduce viscosity as pointed out above. The water-soluble portion of the oil-soluble product appears to be the most effective portion of the dispersant.

In preparation of the magnetic suspensions, the ferromagnetic iron material is prepared in an aqueous medium in the presence of the petroleum sulfonate dispersant by conversion of an iron compound to magnetic iron oxides or hydroxyoxides in the aqueous medium under controlled pH conditions. Apparently, under the controlled pH conditions the formation of iron oxide and conversion to the magnetic form is obtained in proper particle size to obtain a dispersion. At pH below about 5.5, no magnetic product is obtained and at a pH above about 8 the product settles out and no dispersion is obtained.

A convenient method for carrying out the reaction is to dissolve an iron compound in an aqueous medium containing the petroleum sulfonate dispersant and adding an alkali to obtain the required pH conditions to precipitate the iron as iron hydroxide which is converted to a magnetic iron oxide such as magnetite or magnetic hydroxyoxide of iron when the iron is present in both ferric and ferrous states. To obtain the iron in both ferric and ferrous states, the iron may be added in one state and then a portion of the iron converted to the other state. For example, the iron compound may be dissolved in the aqueous medium as a ferrous salt and the alkali added and reaction carried out with agitation in presence of air which is sufficient to oxidize a portion of the iron from the ferrous to the ferric state. In addition to air, other oxidizing agents known to oxidize ferrous iron under alkaline conditions, such as for example hydrogen peroxide, a halogen as chlorine or bromine, and hypochlorite may be added under controlled conditions to provide the relatively mild oxidizing conditions required for the oxidation. When a mixture of ferrous and ferric iron compounds, preferably in proper proportion to obtain the magnetite are used, oxidation is not necessary and the magnetic iron oxides or oxyhydroxides are obtained under the alkaline conditions. When a ferric compound is used by itself, the reaction is carried out under controlled conditions to reduce a portion of the ferric iron to the ferrous state.

Any iron compound which is sufficiently soluble in water to form iron hydroxide upon addition of alkali may be used in the preparation of the magnetic suspensions. Inorganic salts such as chlorides, bromides, nitrates and sulfates are preferred. However, organic iron compound such as the formates or acetates may also be used. It is not necessary to use an iron compound which is completely soluble in water. However, the compound must be at least partially soluble to supply sufficient iron to initiate the reaction which would then permit additional iron to dissolve and react.

In addition to having the iron in solution in the proper ratio of ferrous and ferric iron for the formation of magnetite and/or magnetic oxyhydroxides, theoretically one equivalent of alkali per equivalent of iron is required to convert substantially all of the iron to the magnetic forms. While a significant portion of the iron may be converted to the magnetic form by using as little as ⅓ equivalent of alkali, generally the reaction is carried to the extent that at least 0.8 equivalent of alkali per equivalent of iron has been reacted in maintaining the desired pH conditions. Preferably the reaction is carried to substantial completion which will utilize about 1 equivalent of alkali per equivalent of iron. The alkali is generally added continually or periodically to the solution containing the iron compound and dispersant to maintain the pH of the solution or reaction mixture in the range of 5.5 to 8, preferably in the range of 6 to 7.

Any alkali soluble in water which will provide the hydroxyl groups may be used. The oxides and hydroxides of alkali metals such as sodium, potassium, and lithium are preferred. Ammonium hydroxide and organic hydroxides such as tetramethylammonium hydroxide may also be used. In addition, alkaline earth metal hydroxide and oxides, such as calcium and magnesium hydroxide may be used as well as mixtures of these various alkalies.

The magnetic iron compositions may be obtained under the controlled pH conditions at temperatures below room temperature to elevated temperatures. Preferably the reaction mixture is heated to a temperature of at least 40° C, and generally at a temperature of at least 80° C to obtain a more rapid rate of conversion of the iron or iron hydroxide to the magnetic form. A reaction rate in the range of 90° to 140° C is preferred at which temperature a reaction time of from 15 minutes to four hours is generally sufficient to convert the iron to the magnetic oxide and/or the oxyhydroxide form. While a higher temperature up to about 250° C or higher may be used, the reaction is most conveniently carried out in about 1 to 4 hours at a temperature of 90° to 100° C without the use of pressure equipment. At these temperatures, the rate of reaction is sufficiently rapid and corresponds favorably to the rate of oxidation which can be obtained from ferrous to ferric iron by relatively mild agitation of the reaction mixture in the air to convert most of the iron to the magnetic form. Upon the conversion of the iron hydroxide to magnetite or its magnetic forms, the iron is precipitated in fine particle size which in the presence of the dispersant remains dispersed in the aqueous medium such that suspensions containing up to 30% of the magnetic material may be obtained. These materials do not settle out upon standing and function as magnetic fluids.

In addition to using iron alone, other polyvalent metals such as nickel, manganese and other metals known to form ferrites or magnetic oxy or hydroxy compounds with iron may be used in combination with the iron. These metals as metal compounds may be dissolved in the aqueous medium with iron in the proper proportion for the formation of the ferrite or desired composition and reacted in the manner similar to that used when iron is used alone with some adjustments being made to obtain the optimum formation of the respective metal oxides for the formation of the ferrite or magnetic composition.

A water dispersion of magnetic particles was prepared using a water-soluble, purified petroleum sulfonate. To 250 ml of water, 10 grams of the purified petroleum sulfonate was added and heated to about 90° C. To the hot solution, ferrous sulfate was added in an amount such as to supply one gram of iron. After the ferrous sulfate was dissolved, ferric sulfate hydrate was added in an amount to supply one gram of iron as ferric sulfate. The solution was then neutralized to a pH of about 7 upon addition of sodium hydroxide, as a 50 percent solution. Carbon dioxide free air was then bubbled through this solution while it was heated at 90° for about 2½ hours. Additional amounts of sodium hydroxide were periodically added at this time to maintain the pH at about pH 7. After heating for about 2½ hours, the sample was centrifuged to remove any insolubles. The supernatant liquid obtained was magnetic and was attracted to a magnet when the magnet was placed next to a beaker. Drying of the supernatant liquid gave a tarry substance which was mixed with diatomaceous earth. The product contained 4 percent iron when mixed with the diatomaceous earth, and the magnetization of the product was tested by using a procedure similar to that described by D. F. Evans in the *Journal of Chemical Society* (A), London, 1967, 1670. In the procedure, two similar magnets were fixed in position on the pan of an analytical balance with the north pole of one of the magnets facing the south pole of the other. The pole faces of each of the magnets were square having a dimension of 2.5 cm on edge. The magnets were placed with a pole gap of 3.3 cm at the bottom and 3.5 cm at the top. In determining the magnetic susceptibility, the sample was ground into a fine uniform powder and packed into a Pyrex test tube of the type normally used for nuclear magnetic resonance measurements having an inside diameter of 4 mm. The sample tube was rigidly fixed between and near the top of the two magnets so that the top of the sample in the test tube was about 5 mm below the top of the magnets. The relative magnetic susceptibility was obtained by noting the change in weight of the magnets in the presence of the sample. Samples of about 15 milligrams were tested which filled the test tube to a height of about 3 to 4 mm and the relative magnetic susceptibility was determined by dividing the change in weight of the magnets obtained by the grams of iron in the sample. The strength of the magnetic field in the area of the sample was about 240 oersteds. When so measured, it was found that the product had a magnetization of 3 grams per gram of iron. Three commercial laboratory grade samples of $Fe_3O_4$ or magnetite when measured in the apparatus had magnetizations in the range of from 3.3 to 3.6 grams per gram of iron. A sample of iron of standard of reference grade had a magnetization of 2 grams per gram of iron.

What is claimed is:

1. A process for the preparation of magnetic fluid of a suspension of a ferromagnetic iron material in an aqueous medium which comprises mixing a petroleum sulfonate in the aqueous medium, dissolving an iron compound in the aqueous medium, adding an alkali to the aqueous medium, and reacting the mixture at a pH in the range of 5.5 to 8 to form magnetic iron oxide or magnetic hydroxyoxide, said iron being present in the aqueous medium as ferric and ferrous forms, and said petroleum sulfonate being mixed in an amount sufficient to disperse the iron oxide or iron hydroxide.

2. A process according to claim 1 wherein the mixture is reacted at a temperature in the range of 40° to 250° C.

3. A process according to claim 2 wherein the iron compound is dissolved in the aqueous medium in an amount to form suspensions containing from 5 to 30 weight percent of magnetic iron oxide or hydroxyoxide.

4. A process according to claim 2 wherein the alkali is added to the aqueous medium containing the iron compound to maintain the reaction mixture at a pH in the range of 6 to 7 to convert the iron compound to the magnetic iron material.

5. A process according to claim 4 wherein the mixture is reacted until at least 0.8 equivalent of the alkali for an equivalent of iron has reacted.

6. A process according to claim 5 wherein the alkali is sodium hydroxide and the mixture is heated at a temperature in a range of 90° to 140° C.

7. A process according to claim 6 wherein the iron compound is a mixture of a ferric compound and a ferrous compound.

8. A process according to claim 6 wherein the iron compound is a ferrous salt and is dissolved in the aqueous medium in a sufficient amount to form a suspension containing from 5 to 30 weight percent of magnetic iron oxide or hydroxyoxide.

9. A process according to claim 8 wherein the ferrous salt is ferrous sulfate and the reaction mixture is heated to a temperature in the range of 85° to 100° C with agitation in air to oxidize a portion of the iron from ferrous to ferric state.

10. A process according to claim 9 wherein a compound of a metal selected from the group consisting of nickel and manganese is added with the iron compound to the aqueous medium.

11. A process according to claim 9 wherein the petroleum sulfonate dispersant is the water-soluble portion of the oil-soluble petroleum sulfonate.

12. A magnetic suspension prepared by the process of claim 1.

13. A magnetic suspension prepared by the process of claim 4.

14. a magnetic suspension prepared by the process of claim 6.

15. A magnetic suspension prepared by the process of claim 9.

* * * * *